(12) United States Patent
Kam

(10) Patent No.: US 9,427,242 B2
(45) Date of Patent: Aug. 30, 2016

(54) GUIDE PIN GAUGE

(75) Inventor: Andrew Kam, Odessa, FL (US)

(73) Assignee: LINVATEC CORPORATION, Largo, FL (US)

( * ) Notice: Subject to any disclaimer, the term of this patent is extended or adjusted under 35 U.S.C. 154(b) by 457 days.

(21) Appl. No.: 13/608,499

(22) Filed: Sep. 10, 2012

(65) Prior Publication Data

US 2013/0090658 A1 Apr. 11, 2013

Related U.S. Application Data

(60) Provisional application No. 61/532,521, filed on Sep. 8, 2011.

(51) Int. Cl.
*A61B 17/17* (2006.01)
*A61B 17/16* (2006.01)

(52) U.S. Cl.
CPC ............ *A61B 17/17* (2013.01); *A61B 17/1615* (2013.01); *A61B 17/1714* (2013.01)

(58) Field of Classification Search
CPC ...................... A61B 2019/462; A61B 17/8897
USPC ......... 606/80, 96; 33/512, 542.1, 639, 679.1
See application file for complete search history.

(56) References Cited

U.S. PATENT DOCUMENTS

| | | | | |
|---|---|---|---|---|
| 4,216,585 A * | 8/1980 | Hatter | ...................... | G01B 5/18 33/836 |
| 5,013,318 A * | 5/1991 | Spranza, III | ......... | A61B 5/1076 33/512 |
| 6,494,848 B1 * | 12/2002 | Sommercorn | ..... | A61B 17/0057 33/512 |
| 6,764,453 B2 * | 7/2004 | Meier | .................. | A61B 5/1076 33/512 |
| 8,728,088 B2 * | 5/2014 | LeBeau | .................. | A61B 19/46 606/102 |
| 2006/0106393 A1 * | 5/2006 | Huebner | .............. | A61B 17/164 606/80 |
| 2008/0188935 A1 * | 8/2008 | Saylor | ................ | A61B 17/0401 623/13.14 |
| 2012/0016373 A1 * | 1/2012 | Impellizzeri | .................. | 606/104 |
| 2013/0304068 A1 * | 11/2013 | Larche et al. | ................... | 606/79 |

FOREIGN PATENT DOCUMENTS

WO    WO2010/094846    * 8/2010

* cited by examiner

*Primary Examiner* — David Bates
(74) *Attorney, Agent, or Firm* — Bond, Schoeneck & King, PLLC; Frederick Price

(57) ABSTRACT

A guide pin gauge is described for use in measuring the thickness of an object at a particular location. The guide pin gauge includes a distal cutting head, a proximal shank having an outside diameter equivalent to an outside diameter of said distal cutting head, and a reduced diameter portion extending a length between the distal cutting head and the proximal shank. A proximal facing shoulder is provided at a transition between said distal cutting head and said reduced diameter portion. Markings are provided as a scale along said reduced diameter portion. The distal cutting head may be passed entirely through the hole, and displaced to a side such that a distal extent of the hole engages with the proximal facing shoulder. The markings may then be read to determine a distance to the distal extent of the hole.

8 Claims, 1 Drawing Sheet

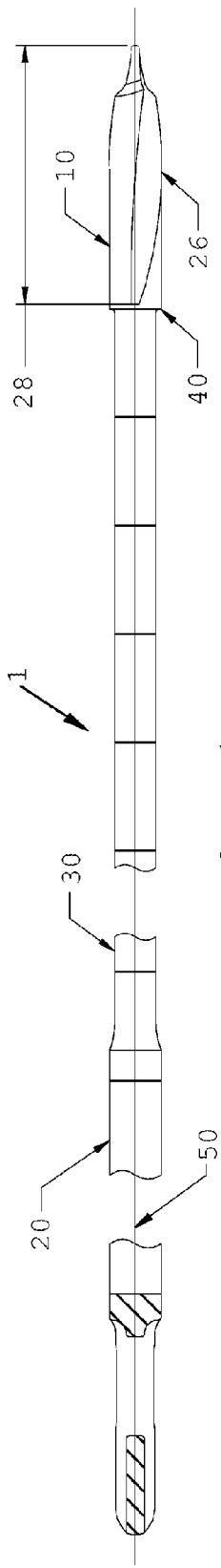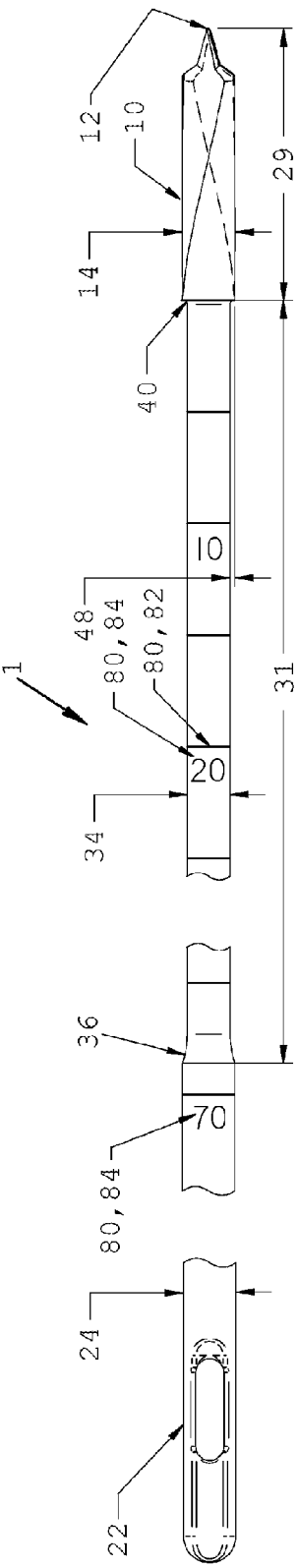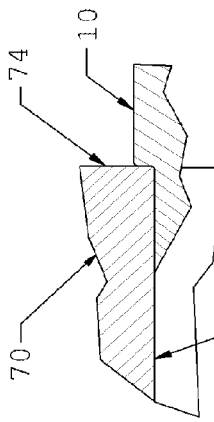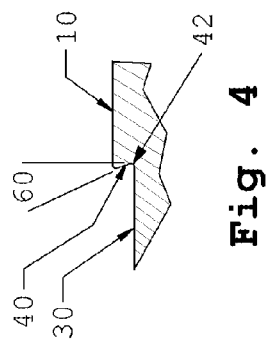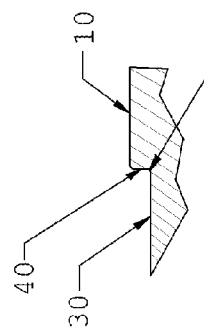

GUIDE PIN GAUGE

CROSS REFERENCE TO RELATED APPLICATIONS

This application is a non-provisional of and claims the benefit of priority from U.S. Provisional Patent Application Ser. No. 61/532,521, entitled "GUIDE PIN GAUGE", and filed on 8 Sep. 2011. The content of the above-identified application is incorporated herein by reference in its entirety.

TECHNICAL FIELD OF THE INVENTION

This invention relates to the design and use of a surgical instrument. The present invention relates more specifically to a surgical guide pin suitable for use in arthroscopic surgical procedures.

BACKGROUND OF THE INVENTION

Orthopedic surgeons utilize guide pins for a variety of common procedures, most involving a repair of a joint. For example, when securing a graft in the knee to replace anterior crucial ligament, a guide pin is often used to help create precisely located tunnels for the passage of a graft and/or suture material.

Because the location of such tunnels is critical to the success of any procedure, the guide pins are held along an axis inside of a drill guide or a cannulated reamer, which the drill guide or cannulated reamer is aligned at a specific, desired angle to the joint. The guide pin is then driven by a conventional surgical drill into a first bone, such as the tibia. Once through the tibia, a reamer is often passed over the guide pin to complete the tunnel through the tibia. Afterword, another guide device is often used to axially position the guide pin for passage into a second bone, such as the femur. The conventional surgical drill is then used to drive the guide pin into the femur. Lastly, as is relevant to the present invention, a reamer is then again passed over the guide pin to complete a tunnel through the femur.

As mentioned above, the placement of guide pin is critical, because the ultimate location of the necessary tunnels is a direct result of a proper placement of the guide pins. While the drill guides and other placement devices can be used to accurately determine an initial location and various angle from that placement, once the guide pin enters bone, there is little that can be done to accurately determine the relationship between the distal extent of the guide pin in relation to the extents of the bone or other layers of tissue. Further complicating this is a general inability to accurately determine bone and other tissue thickness in a particular direction along the axis of the desired tunnel.

To aid in the proper placement of the guide pin, certain devices have been invented that allow the surgeon to see graphical representations of a placement. As it is impractical to utilize a real visualization, such as through the use of a magnetic or x-ray device, the graphical visualizations are simulated and based on previously obtained images. As can be easily imagined, such system require highly accurate instrumentation and sensors to know the placement of the surgical instruments and they require perfectly scaled and accurate images of the patients joint for the graphical representation to be functional.

It is also known for a surgeon to merely drive a drill guide by tactile feel and then withdraw the guide pin at times for the purpose of obtaining depth or thickness measurements using traditional measurement tools. While this method is reasonably reliable, it can be time consuming for the removal and replacement of the guide pin and surgical drill, and such a method creates additional clutter in the operating room environment.

The inventors found that placing gradations on the outside of a traditional guide pin failed to provide a suitable measurement regarding a thickness of a tunnel or hole, because once the hole or tunnel is completed, meaning once the guide pin passes entirely through a bone, any gradations starting at the distal end of the guide pin are useless.

Further, the inventors discovered that the mere placement of a proximal facing shoulder near the distal end of the guide pin resulted in problems with accuracy and equipment. For example, the inventor discovered that to create the proximal facing shoulder, the head must be significantly larger than the shaft resulting in a loose fit of the shaft while in a drill guide, cannulated reamer, or an oversized resulting hole due to an oversized head. The inventors discovered that significant accuracy in the placement of the guide pin is lost when using either of these options. Such loss in accuracy would not be tolerated by surgeons or patients.

SUMMARY OF THE INVENTION

The present invention attempts to provide a means for measuring thickness or placement of a surface at a distal side of hole without creating the accuracy degrading problems identified by the inventor.

In accordance with one embodiment of the present invention a guide pin gauge is provided comprising a distal cutting head, a proximal shank, and a reduced diameter portion extending a length between the distal cutting head and the proximal shank. A proximal facing shoulder is provided at a transition between the distal cutting head and the reduced diameter portion. Markings are provided as a scale along said reduced diameter portion. An outside diameter of said distal cutting head and an outside diameter of said proximal shank are equivalent.

In accordance with one embodiment of the invention, the distal cutting head further comprises cutting surfaces comprising flutes. The flutes extend proximally and terminate a distance distally from said proximal facing shoulder. Preferably, each of the flutes reduce in depth as that flute extends proximally toward said proximal facing shoulder.

In accordance with one embodiment of the invention, the proximal facing shoulder is arranged perpendicular to a longitudinal axis of said guide pin gauge. In accordance with another embodiment, the proximal facing shoulder is arranged to form an acute angle with the reduced diameter portion.

In accordance with one embodiment of the present invention, the scale is indexed such that the origin of the scale is at said proximal facing shoulder. The guide pin gauge may further comprise markings provided as a second scale, the second scale being indexed such that the origin of the second scale is at a distal extent of the distal cutting head.

BRIEF DESCRIPTION OF THE DRAWINGS

So that the manner in which the features of the present invention can be understood in detail, a more particular description of the invention briefly summarized above may be had by through the detailed description with reference to the attached figures. It is to be noted, however, that the figures illustrate only typical embodiments of this invention and are therefore not to be considered limiting of its scope, for the invention may admit to other equally effective embodiments. Moreover, the figures are not necessarily to scale, with emphasis generally being placed upon illustrating the principles of certain embodiments of invention.

Thus, for further understanding of the nature and objects of the invention, references can be made to the following figures in which:

FIG. 1 is a left side, partially sectioned view of an embodiment made in accordance with the present invention;

FIG. 2 is a top view of the embodiment shown in FIG. 1;

FIG. 3 is an enlarged and sectioned view of the proximal facing shoulder of the embodiment shown in FIGS. 1 and 2;

FIG. 4 is an enlarged and sectioned view of an alternate embodiment of a proximal facing shoulder of FIGS. 1, 2 and 3; and FIG. 5 is an enlarged sectional view of the embodiment of of FIGS. 1, 2 and 3 while engaged at a distal extent of a hole.

DETAILED DESCRIPTION

Referring to FIGS. 1, 2, 3, 4, and 5 together, a guide pin gauge 1 of the present invention includes a distal cutting head 10, a proximal shank 20 and a reduced diameter portion 30 located extending a distance 31 between the distal cutting head 10 and the proximal shank 20. A proximal facing shoulder 40 is positioned at a transition between the distal cutting head 10 and the reduced diameter portion 30. The proximal facing shoulder 40 may be perpendicular to a longitudinal axis 50 of the guide pin gauge 1, as is represented in FIG. 3, while the proximal facing shoulder 40 may also be provided with an angle 60 off of perpendicular (to the longitudinal axis 50) and forming an acute angle with the reduced diameter portion 30 for the purpose of more solidly engaging a distal extent 74 of a hole 72 within an object 70, such as a bone, cannulated reamer or the like. A radius 42 may be may be placed at an intersection between the proximal facing shoulder 40 and the reduced diameter portion 30.

Counting from the proximal facing shoulder 40, the guide pin gauge 1 includes markings 80 representative of a scale. The scale may include annular rings 80,82 at regular intervals, with at least some of the rings 80,82 further including associated numerical indicators 80,84. The regular intervals may be spaced according to the metric, imperial or any other system of units. The rings 80,82 may not encircle the entire diameter. For example, one side of the guide pin gauge may include a scale arranged in accordance with the metric system while the other side is arranged in accordance with another system of units. Further, one side of the guide pin gauge 1 may include a scale indexed as beginning at the proximal facing shoulder 40 while another side of the guide pin gauge may include a scale indexed as beginning at a distal tip 12 of the distal cutting head 10. Regardless of arrangement, the rings 80,82 and numerical indicators 80,84 may be laser etched onto the surface of the guide pin gauge 1, and may be mechanically added through the use of rollers or the like. While not preferred, the markings 80 may be placed with an ink or paint.

The rings 80,82 and numerical indicators 80,84 may preferably extend along the length 31 of the reduced diameter portion 30 and further extend along the proximal shank 20. It may not be advantageous to extend the rings 80,82 and numerical indicators 80,84 along the entire length of the proximal shank 20, due at least in part to the fact that it is unlikely that a majority of the proximal shank 20 will be placed in a hole for measurement purposes. Instead, at least a portion of the proximal shank 20 includes a drive feature 22.

An important feature of the present invention lies in the fact that an outside diameter 14 the distal cutting head 10 and an outside diameter 24 of the proximal shank 20 are equivalent, with the term "equivalent" being used in the specification and claims as being the same except for typical manufacturing tolerances causing slightly different diameters, and outside diameters 14,24 being sufficiently larger than an outside diameter 34 of the reduced diameter portion 30 to produce a sufficient height 48 for the proximal facing shoulder 40. As the inventors discovered, having an enlarged diameter cutting head 10 without an equivalently sized proximal shank 20 may result in inaccurate placement of a cannulated reamer due to a clearance between an inside diameter of a the cannulated reamer and the reduced diameter portion 30 when the cannulated reamer is not otherwise supported. In other words, the proximal shank 20 of the present invention was found to provide additional support to a cannulated reamer being passed there over and/or to the guide pin gauge 1 as it is passed through a drill guide. With such support, the supported cannulated reamer will proceed in a straighter path along the guide than if the proximal support 20 where provided with a diameter smaller than the diameter 14 of the distal cutting head 10. Further, the proximal shank 20 will remain at least partially engaged with a drill guide during passage of the distal cutting head 10 from the drill guide and into a bone, further maintaining the accuracy currently enjoyed by surgeons using the present guide pin 1 without a reduced diameter portion and accompanying gauge.

The distal cutting head 10 of the guide pin gauge 1 may include cutting surfaces 26 that are somewhat typical to more traditional guide pins. It is envisaged, however, that the cutting surfaces 26 may be arranged in a slightly less aggressive manner due to a reduced torque capacity of the guide pin gauge 1 because of the reduced diameter portion 30. Further, the cutting surfaces 26 may include flutes extending a length 28 that is shorter than an overall length 29 of the distal cutting head 10 to provide a more consistent shoulder 40, the more consistent proximal facing shoulder 40 functioning more reliably than if flutes extended through the shoulder 40 causing voids in the shoulder 40. Further, manufacturing the cutting surfaces 26 such that flutes become shallower toward and ultimately terminate before the shoulder 40, may result in a higher overall torque capacity of the guide pin gauge 1.

To reduce torsional stress concentrations caused by the reduced diameter portion 30, it is preferred that a transition 36 between reduced diameter portion 30 and the proximal shank 20 be provided with a radius (as shown) or a chamfer (not shown). Similarly, a transition between the proximal shoulder 40 and the reduced diameter portion 30 may be provided with a radius 42. The radius 42 at the transition between the reduced diameter portion 30 and the proximal facing shoulder 40 is preferably smaller than that of the radius 36 at the transition between the reduced diameter portion 30 and the proximal shank 20 because of the need to have the proximal facing shoulder 40 be well defined.

Because of the relatively small diameter of the present invention, the proximal shank 20 of the guide pin gauge 1 may include drive features 22, such as indentations and passageways that facilitate a transfer of torque from drill motor to the guide pin gauge 1. Any of the known indentations, passageways or other known features may work well.

The guide pin gauge 1 of the present invention may be made of any of the known drill materials, with the preferred material being 17-4PH stainless steel UNS 517400, condition H900 per ASTM A564 Min Hardness 40 Rc.

In a preferred embodiment, the diameter 34 of the reduced diameter portion 30 is 0.075" while the diameter 14 of the distal cutting head 10 and the diameter 24 of the proximal shank 20 are preferably 0.093". While the relationship between the diameters may change, it is important to provide the reduced diameter portion 30 with a diameter 34 sufficient to transfer the torque requirements of the cutting head without plastic deformation or failure. It may be possible to reduce the length 31 of the reduced diameter portion 30 in exchange for a further reduced diameter and vice versa. While the above are dimensional characteristics of a preferred embodiment, it should be understood that the dimensions may be scaled or otherwise altered according the desired size of the hole to be created. It should further be understood that larger diameters, while still retaining the reduced diameter portion 40 for reasons of gauging, may result in more accurate placement of the desired holes.

The invention claimed is:

1. A guide pin gauge comprising:
   a distal cutting head;
   a proximal shank;
   a reduced diameter portion extending a length between and connecting the distal cutting head and the proximal shank;
   a proximal facing shoulder provided at a transition between said distal cutting head and said reduced diameter portion that is adapted to engage the distal extent of a hole; and
   markings provided as a scale on said reduced diameter portion, said markings indexed to be fixed at zero at the proximal facing shoulder and increasing toward the proximal shank to measure a distance proximally from the distal extent of the hole that is engaged by the proximal facing shoulder;
   wherein an outside diameter of said distal cutting head and an outside diameter of said proximal shank are equivalent.

2. The guide pin gauge of claim 1 wherein the distal cutting head further comprises cutting surfaces comprising flutes, the flutes extending proximally from a tip of the distal cutting head and terminating a distance distally from said proximal facing shoulder.

3. The guide pin gauge of claim 1 wherein the proximal facing shoulder is arranged perpendicular to a longitudinal axis of said guide pin gauge.

4. The guide pin gauge of claim 1 wherein the proximal facing shoulder is arranged to form an acute angle with said reduced diameter portion.

5. The guide pin gauge of claim 4 further comprising markings provided as a second scale, the second scale being indexed such that the origin of the second scale us at a distal extent of said distal cutting head.

6. The guide pin gauge of claim 2 wherein the flutes reduce in depth as the flute extends proximally toward said proximal facing shoulder.

7. The guide pin gauge of claim 1 further comprising a radiused transition between said reduced diameter portion and said proximal shank.

8. A guide pin gauge comprising:
   a distal cutting head comprising fluted cutting surfaces extending proximally from a tip of the distal cutting head and terminating a distance distally from a proximal facing shoulder that is adapted to engage the distal extent of a hole, said fluted cutting surfaces reducing in depth as the flute extends proximally toward said proximal facing shoulder;
   a proximal shank;
   a reduced diameter portion extending a length between the distal cutting head and the proximal shank;
   said proximal facing shoulder provided at a transition between said distal cutting head and said reduced diameter portion, said proximal facing shoulder being one of (i) perpendicular to a longitudinal axis of said guide pin gauge and (ii) forming an acute angle with said reduced diameter portion; and
   markings provided as a scale along said reduced diameter portion, said markings indexed to be zero at the proximal facing shoulder and increasing toward the proximal shank to measure a distance proximally from the distal extent of the hole that is engaged by the proximal facing shoulder,
   wherein an outside diameter of said distal cutting head and an outside diameter of said proximal shank are equivalent.

* * * * *